United States Patent [19]

Planker et al.

[11] Patent Number: 5,616,799
[45] Date of Patent: Apr. 1, 1997

[54] PROCESS FOR THE PREPARATION OF GLYCOLOYLANILIDES

[75] Inventors: Siegfried Planker, Königstein; Theodor Papenfuhs, Frankfurt, both of Germany

[73] Assignee: Hoechst Aktiengesellschaft, Germany

[21] Appl. No.: 423,522

[22] Filed: Apr. 17, 1995

[30] Foreign Application Priority Data

Apr. 19, 1994 [DE] Germany ............... 44 13 618.8

[51] Int. Cl.$^6$ ............... C07C 233/33; C07C 231/02
[52] U.S. Cl. ............... 564/202; 558/415; 558/416; 560/45; 562/452; 562/455; 564/86; 564/142; 564/156; 564/200; 564/201; 564/395; 564/396; 564/397; 564/398
[58] Field of Search .................. 564/142, 200, 564/201, 202, 395, 396, 397, 398, 86, 156; 558/415, 416; 560/45; 562/452, 455

[56] References Cited

U.S. PATENT DOCUMENTS

| | | | |
|---|---|---|---|
| 4,334,073 | 6/1992 | Diehr | 546/245 |
| 5,177,261 | 1/1993 | McCarthy et al. | 564/153 |

FOREIGN PATENT DOCUMENTS

| | | | |
|---|---|---|---|
| 4003078 | 2/1990 | Germany | 564/398 |

*Primary Examiner*—Shailendra Kumar
*Attorney, Agent, or Firm*—Connolly & Hutz

[57] ABSTRACT

A process for the preparation of glycoloylanilide of the formula (G)

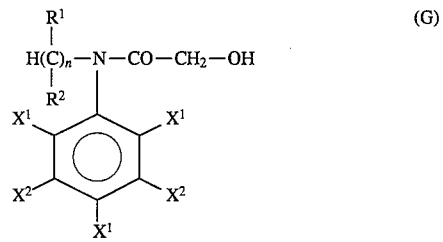

is recited that involves reacting a nitrobenzene with hydrogen and, if desired, with a carbonyl compound, in the presence of a noble metal catalyst and a solvent, reacting the compound produced with chloroacetyl chloride, reacting the resulting product with a benzyl alcohol and with a base, or reacting the resulting compound with an O-benzylglycoloyl chloride, and debenzylating the resulting benzylglycoloylanilide product by reacting with hydrogen in the presence of a noble metal catalyst. The invention also relates to a process for the preparation of O-benzylglycoloylanilide.

47 Claims, No Drawings

PROCESS FOR THE PREPARATION OF GLYCOLOYLANILIDES

The present invention relates to processes for the preparation of glycoloylanilides (hydroxyacetanilides) and to new O-benzylglycoloylanilides and processes for their preparation.

Glycoloylanilides are important precursors for the preparation of herbicides (EP-A 300 344 and EP-A 510 479), pharmaceutical active compounds (DE-A 083 964 and EP-A 284 388) and fungicides (US 4 440 780).

A variety of methods has already been described for their preparation.

According to US 4 440 780 (Example 3) a chloroacetanilide is hydrolyzed with aqueous alkali metal hydroxide in the presence of a solvent (dimethoxyethane). This hydrolysis is followed by a very complex, multistage workup which comprises, inter alia, three filtration steps, two extraction steps and two drying steps and the passing through of gaseous HCl. The corresponding glycoloylanilide is obtained in a yield of 78.1%, with no information being given about the purity of the product.

The general application of this process is countered not only by the unsatisfactory yield and very complex workup but also by the unwanted formation of corresponding ethers which, under the conditions of this hydrolysis, are formed from glycoloylanilide which has already been formed and from chloroacetanilide which is not yet reacted, and lead to a considerable reduction in the yield. The formation of these ethers, however, is inevitable or can be avoided only to an extremely small extent.

DE-A 32 22 229 describes a process for the preparation of mono- and disubstituted glycoloylamides (glycolic acid amides), in which a mixture of sodium chloroacetate, a tertiary amine as catalyst and xylene as diluent is heated to boiling, the solid intermediate formed in the process is isolated, and this solid product, whose structure is not disclosed but which is presumably a mixture of oligoglycolides, is reacted with a primary or secondary amine in the presence of a quaternary ammonium salt as catalyst to give the corresponding glycoloylamides.

The yields, when (cyclo)aliphatic amines are employed, are moderate to acceptable; in the only example relating to a glycoloylanilide in which figures are given (Table 1, Example 6, using N-methylaniline), however, a yield of only 62% is indicated.

Disadvantages of this process are that the solid oligoglycolide product mixture has to be isolated by filtration and that it is employed as a chlorine-containing product in the subsequent process step. In addition, the use of quaternary ammonium salts as catalyst presents problems owing to the biocidal properties thereof. Furthermore, the yield for a preparation of glycoloylanilides is unsatisfactory.

DE-A 29 04 490 relates to a process for the preparation of glycoloylamides (α-hydroxycarboxamides) by reacting α-halocarboxamides with alkali metal acetates or alkaline earth metal acetates to give the corresponding α-acetoxycarboxamides, followed by cleavage (deacylation) of the α-acetoxycarboxamides. However, the α-halocarboxamides used as starting materials must be prepared independently by, for example, reacting α-halocarbonylhalides with ammonia and/or primary or secondary a mines, if desired in the presence of an acid acceptor (potassium hydroxide). Despite the use of α-halocarboxamides as starting material, the process of DE-A 29 04 490 is a two-stage process in which the α-acetoxycarboxamide formed in the first process stage has to be isolated, with separation of the solvent, so that subsequently, in the second process stage, it can be cleaved by solvolysis using an aliphatic alcohol as solvent in the presence of catalytic amounts of an alkali metal hydroxide or alkaline earth metal hydroxide.

Where indicated, the yields are high (from 90 to 99%) even with the use of aromatic amines, although the purity achieved, at 97.3 or 98%, respectively (GC), leaves room for improvement.

Disadvantages of the process are on the one hand the use of α-halocarboxamides, whose preparation requires a separate operation, as starting material and on the other hand, the use of at least two different solvents, the isolation of the α-acetoxycarboxamide and the use of quaternary ammonium salts as catalysts. The acetic ester, which is formed in stoichiometric quantities as a result of the reaction which takes place in the second stage, like the biocidal quaternary ammonium salt used as catalyst, makes it necessary both when working up and for disposal to employ additional process steps which increase the apparatus required.

There is therefore considerable interest in the provision of a process which avoids the disadvantages of the processes described above and which is simple to carry out industrially. In addition such a process should permit broad application and should enable the preparation of glycoloylanilides not only in high yields but also in high purity.

This object is achieved by a process for the preparation of glycoloylanilides of the formula (G)

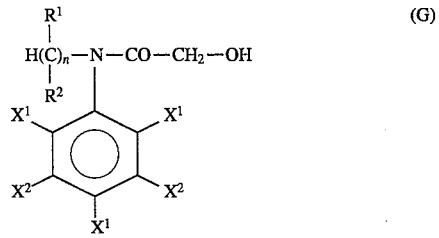

(G)

This process comprises reacting a nitrobenzene of the formula (A) in which $X^1$ independently at each occurrence is H, halogen, cyano, trifluoromethyl, alkyl or alkoxy having in each case 1 to 4 carbon atoms in the alkyl moiety, and $X^2$ independently at each occurrence is H, halogen, cyano, carboxyl, trifluoromethyl, substituted or unsubstituted aminocarbonyl or aminosulfonyl, alkyl, alkoxy or alkoxycarbonyl having in each case 1 to 4 carbon atoms in the alkyl moiety, and n is 0 or 1, with hydrogen and, if desired, with a carbonyl compound of the formula (B) in which $R^1$ and $R^2$ are H, alkyl, hydroxyalkyl, alkoxyalkyl or acyloxyalkyl having in each case 1 to 4 carbon atoms in the alkyl moiety, in the presence of a catalyst which comprises noble metal and of a solvent, in accordance with reaction equation (1)

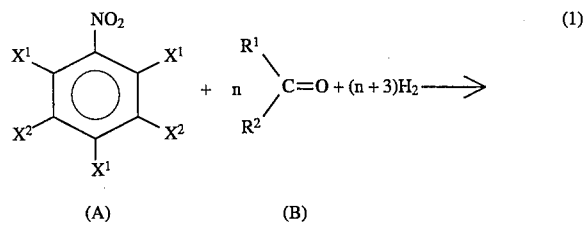

(1)

-continued

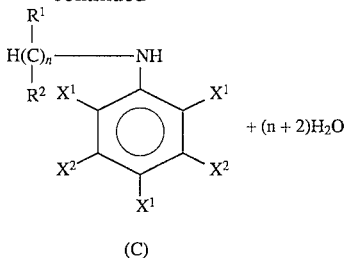

separating off the catalyst and reacting the compound of the formula (C) with chloroacetyl chloride, in accordance with reaction equation (2)

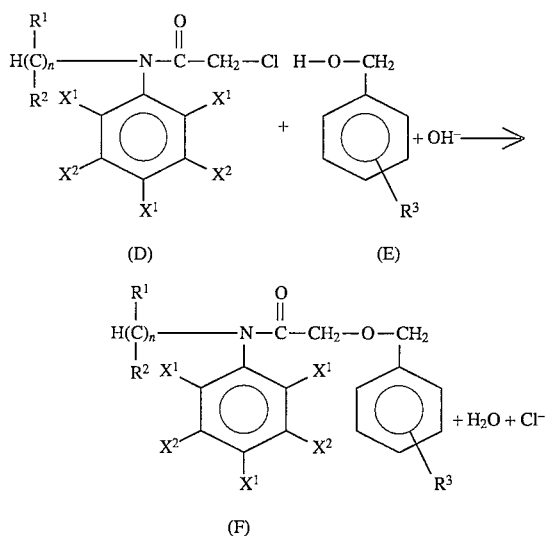

to give a compound of the formula (D), separating off the hydrogen chloride formed, reacting the compound of the formula (D) with a benzyl alcohol of the formula (E) in which $R^3$ is H, halogen, alkyl or alkoxy having in each case 1 to 4 carbon atoms, and with a base, in accordance with reaction equation (3)

separating off if desired the salt formed from the base and hydrogen chloride, or reacting the compound of the formula (C) with an O-benzylglycoloyl chloride of the formula (K) in which $R^3$ is as defined above, and if desired with a base, in accordance with reaction equation

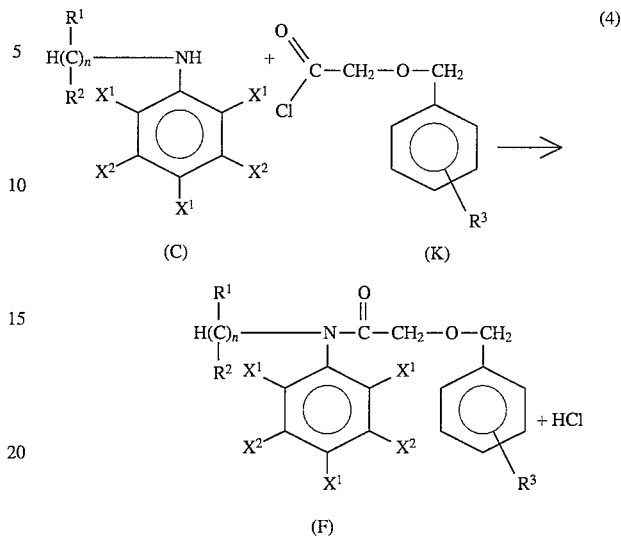

separating off if desired the salt formed from the base and hydrogen chloride, and reacting the O-benzylglycoloylanilide of the formula (F), in the presence of a catalyst which comprises noble metal, with hydrogen, in accordance with reaction equation (5)

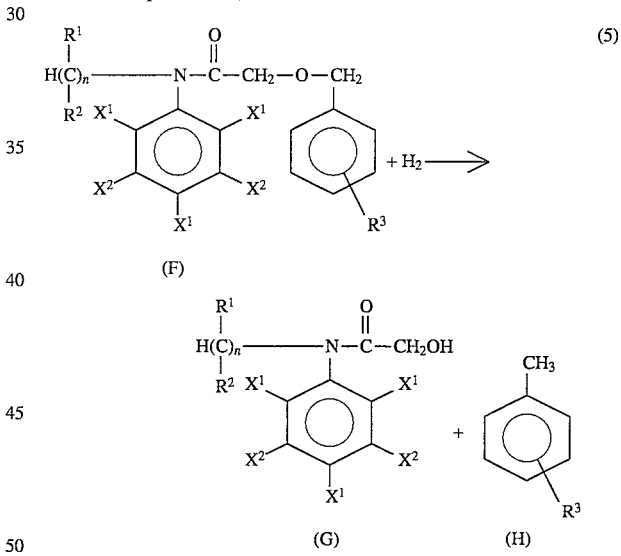

separating off the compound of the formula (H) which is formed and isolating the glycoloylanilide of the formula (g).

One advantage of the process according to the invention is that because of the large number of nitrobenzenes of the formula (A) which are suitable for use it is suited to broad application and leads to a large number of corresponding glycoloylanilides. The process therefore provides a high degree of flexibility.

Although the process according to the invention involves a number of stages, surprisingly it gives the desired glycoloylanilides not only in a very high yield but also in very high purity. Yields of 90% or more can easily be achieved, with the end product being obtained in a purity of 98.5% or more. These results at the same time demonstrate that, despite the sensitivity of glycoloylanilides to hydrolytic influences, there is surprisingly no yield-reducing hydrolytic cleavage of the glycoloylanilides into hydroxyacetic acid and the corresponding aniline.

A further advantage of the process according to the invention is that it is unnecessary to isolate and purify each individual intermediate formed in the course of the synthesis so that it can be processed further in purified form thereafter. Instead, it is possible as desired or required to omit one or more of these isolation steps and the following purification of the particular intermediate. The consequence of this is that the corresponding reaction steps in the process according to the invention have a particularly simple industrial configuration and the process can be carried out without any great complexity.

In the most favorable case the process according to the invention can be carried out, starting from the corresponding nitrobenzene of the formula (A) and using a single solvent, in the manner of a one-pot process, in which all of the reaction stages are gone through, right up to the glycoloylanilide, without isolation and purification of the respective intermediates. This process variant constitutes a particularly advantageous embodiment of the process according to the invention, which embodiment is easy to carry out industrially, and requires only the isolation of the catalyst which comprises noble metal and, if desired, of the salts formed, for example by filtration, and the removal of any water of reaction which is present as a heterogeneous phase. If the catalyst which comprises noble metal is employed in the form of a fixed bed, then its isolation from the respective reaction mixture is also dispensed with.

A large number of different nitrobenzenes are suitable as the nitrobenzene of formula (A). Suitable examples are the various isomeric nitroalkylbenzenes, especially nitrotoluenes, nitroethylbenzenes, nitroxylenes and nitrotrimethylbenzenes, the various isomeric nitrohalobenzenes, nitrodihalobenzenes, nitrotrihalobenzenes and nitrotetrahalobenzenes, the various isomeric nitroanisoles, nitrophenetoles, nitrodimethoxybenzenes and nitrotrimethoxybenzenes, the various isomeric nitrocyanobenzenes and nitrotrifluoromethylbenzenes, the various isomeric nitrobenzoic acids, nitrophthalic acids, nitroisophthalic acids and nitroterephthalic acids and their alkyl esters and unsubstituted or alkyl-substituted amides, and also the various isomeric, unsubstituted or N-alkylsubstituted nitrobenzenesulfonamides.

In general, suitable nitrobenzenes of the formula (A) are those in which $X^1$ independently at each occurrence is H, fluorine, chlorine or trifluoromethyl and $X^2$ independently at each occurrence is H, fluorine, chlorine, trifluoromethyl or substituted or unsubstituted aminocarbonyl.

The criterion of suitability is well met by the various isomeric monohalonitrobenzenes and dihalonitrobenzenes, the various isomeric trifluoromethylnitrobenzenes and the various isomeric nitrobenzenemonocarboxylic acids and nitrobenzenedicarboxylic acids, and also their alkyl esters and unsubstituted or N-substituted amides.

Of particular suitability are the various isomeric monochloro-and monofluoronitrobenzenes, the various isomeric nitrobenzotrifluorides and the various isomeric nitrobenzamides and nitrobenzenedicarboxamides, especially 4-chloro- and 4-fluoronitrobenzene, 4-nitrobenzotrifluoride and 5-nitroisophthalamides.

The nitrobenzene of the formula (A) is reacted with hydrogen and, if desired, with a carbonyl compound of the formula (B) in the presence of a catalyst which comprises noble metal and a solvent at from 0.1 to 5 MPa, in particular from 0.2 to 3 MPa. It is also possible to carry out the reaction at higher pressures, although it will generally be carried out within the abovementioned pressure ranges for reasons of greater ease of an industrial procedure.

Suitable carbonyl compounds of the formula (B) are aliphatic carbonyl compounds, especially acetaldehyde, propionaldehyde, acetone, methyl ethyl ketone, methoxyacetaldehyde and/or acetoxyacetaldehyde, preferably acetaldehyde and/or acetone.

The nitrobenzene of the formula (A) and the carbonyl compound of the formula (B) are employed in a molar ratio of 1: (1.0 to 3.5), in particular 1: (1.01 to 2.5) and preferably 1: (1.05 to 1.5).

The catalyst which comprises from 1 to 10% by weight, preferably from 2 to 5% by weight, of noble metal is employed in a quantity of from 0.01 to 0.3 part, in particular from 0.025 to 0.15 part, by weight of noble metal, based on 100 parts of nitrobenzene of the formula (A).

The reaction of the nitrobenzene of the formula (A) which takes place in accordance with reaction equation (1) is particularly simple to carry out using a supported catalyst which comprises noble metal and which can be employed either in suspended form or as a fixed bed catalyst. Suitable support materials are $Al_2O_3$, pumice, argillaceous earths, silicic acid, kieselguhr, silica gel, $SiO_2$ and/or active charcoal, preferably active charcoal.

The supported catalyst which comprises noble metal usually contains from 1 to 10% by weight, in particular from 2 to 5% by weight, of noble metal, based on the overall catalyst. A recommended catalyst which comprises noble metal is a palladium- or platinum- containing catalyst, especially a supported catalyst which comprises palladium or platinum, if desired in sulfited or sulfided form, and preferably an active charcoal catalyst which comprises palladium or platinum, if desired in sulfited or sulfided form. The choice of the catalyst which comprises noble metal also depends to a certain extent on the nature of the nitrobenzene of the formula (A). Catalysts suitable for the reaction of halogen-free nitrobenzenes are palladium- or platinum-, especially palladium-containing, catalysts, preferably supported catalysts of this kind and, with particular preference, catalysts of this kind supported on active charcoal. If, however, a halogen-containing nitrobenzene of the formula (A) is employed then use will be made, in order reliably to avoid elimination of halogen, of special modified catalyst types, for example a sulfited or sulfided platinum or palladium catalyst, in particular a sulfited platinum catalyst and preferably a sulfited platinum-active charcoal catalyst.

Suitable solvents which may be mentioned are aromatic compounds, for example toluene, the various isomeric xylenes and mixtures thereof, halobenzenes, the various isomeric halotoluenes and dihalobenzenes and mixtures thereof, the various isomeric methoxytoluenes and trimethylbenzenes and mixtures thereof. Furthermore, in the hydrogenation stages alcohols such as methanol, ethanol, the isomeric propanols and butanols and their acetates can be used as solvents. Highly suitable solvents in all stages are toluene, the various isomeric xylenes and mixtures thereof, the various isomeric halotoluenes or methoxytoluenes and mixtures thereof. A particularly simple embodiment of the process according to the invention is one in which the compound (toluene derivative) of the formula (H), which forms in accordance with reaction equation (5), is employed as solvent.

The nitrobenzene of the formula (A) is reacted in accordance with reaction equation (1) normally at from 20°0 to 100° C., in particular at from 60° to 90° C. The reaction results in the formation of the compound of the formula (C). The catalyst and any water of reaction which is present as a heterogeneous phase are separated off and, if desired, the compound of the formula (C) is isolated, for example by distilling off the solvent, before being employed in the subsequent reaction stage. In accordance with a particular process variant only the catalyst and any water of reaction which may be present as a heterogeneous phase are separated off, and the reaction mixture comprising the compound of the formula (C) is reacted directly, without isolating the compound of the formula (C), with chloroacetyl chloride in accordance with reaction equation (2).

The compound of the formula (C) is reacted at from 0° to 150° C., in particular from 20° to 100° C., with chloroacetyl chloride. In general the compound of the formula (C) and chloroacetyl chloride are employed in a molar ratio of 1:(1.0 to 1.5). In a number of cases it has proven useful to employ the compound of the formula (C) and chloroacetyl chloride in a molar ratio of 1:(1.05 to 1.15).

Hydrogen chloride is formed during the reaction and must be separated out of the reaction mixture. This can be done by boiling it off and/or by adding a base, for example an alkali metal hydroxide or alkali metal carbonate. It has proven particularly appropriate to boil off the hydrogen chloride formed.

When the reaction is over, the resulting compound of the formula (D) can be isolated before being employed in the subsequent reaction stage. However, it is advantageous to react the reaction mixture comprising the compound of the formula (D) directly, without isolating the compound of the formula (D), with the benzyl alcohol of the formula (E) in accordance with reaction equation (3).

The benzyl alcohol compound used has the formula (E), in which $R^3$ is H, halogen, alkyl or alkoxy having in each case 1 to 4 carbon atoms, especially H, chlorine, methyl or methoxy.

Generally the compound of the formula (D) and the benzyl alcohol of the formula (E) are employed in a molar ratio of 1:(1 to 1.5). In a number of cases it has been found to be sufficient to react the compound of the formula (D) and the benzyl alcohol of the formula (E) in a molar ratio of 1:(1.02 to 1.2). The compound of the formula (D) is usually reacted at from 20° to 200° C. In a number of cases it is sufficient to carry out this reaction at from 20° to 150° C. The reaction of the compound of the formula (D) is performed in the presence of a base. Generally, the compound of the formula (D) and the base are reacted in a molar ratio or in a ratio of their equivalents of 1:(1.0 to 1.5), in particular 1:(1.02 to 1.2). An alkali metal hydroxide or an alkali metal carbonate is usually used as base.

In this way the compound of the formula (F) is obtained.

Alternatively, the O-benzylglycoloylanilide of the formula (F) can be prepared by reacting the compound of the formula (C) with an O-benzylglycoloyl chloride of the formula (K) in which $R^3$ is as defined above and in particular is H, chlorine, methyl or methoxy, in accordance with reaction equation (4) and, if desired, with the addition of a base. To this end it is possible to react either the compound (C) in isolated form or the reaction mixture comprising the compound of the formula (C), directly, without isolating the compound of the formula (C), with the O-benzylglycoloyl chloride of the formula (K). In this case the catalyst which comprises noble metal and any water of reaction which is produced as a heterogeneous phase are separated off beforehand.

The O-benzylglycoloyl chloride of the formula (K) which is employed in this process variant can be synthesized by known methods, for example by reacting chloroacetic acid with an alkali metal salt of a benzyl alcohol and then chlorinating the O-benzylglycolic acid using phosphorus pentachloride (Helv. Chim. Acta 1933, 16, 1130 to 1132) or by reacting sodium chloroacetate with a benzyl alcohol and then chlorinating the O-benzylglycolic acid with thionyl chloride, phosgene or phosphorus oxychloride.

For the reaction in accordance with equation (4) the compound of the formula (C) and the O-benzylglycoloyl chloride of the formula (K) are employed in a molar ratio of 1:(1 to 1.5), in particular 1:(1.05 to 1.15).

The compound of the formula (C) is generally reacted with benzylglycoloyl chloride of the formula (K) at from 20° to 150° C. In numerous cases it has proven appropriate to carry out this reaction at from 50° to 130° C. During the reaction of the compound of the formula (C) with the O-benzylglycoloyl chloride of the formula (K), hydrogen chloride is formed which must be separated out of the reaction mixture. The separation of the hydrogen chloride can be effected by boiling it out and/or by adding a base.

It is possible to react the compound of the formula (C) with the O-benzylglycoloyl chloride of the formula (K) with the addition of an alkali metal hydroxide and/or alkali metal carbonate as base. In this way the hydrogen chloride formed is converted actually during the reaction into a salt which is, if desired, removed from the resulting reaction mixture, for example by filtration.

For the purpose of further processing, regardless of the mode of preparation, the O-benzylglycoloylanilide of the formula (F) can be isolated or, preferably, the reaction mixture comprising the O-benzylglycoloylanilide of the formula (F) can be reacted directly, without isolating the O-benzylglycoloylanilide of the formula (F), with hydrogen in accordance with reaction equation (5). This reaction uses from 1 to 10% by weight, in particular from 2 to 5% by weight, of catalyst which comprises noble metal in a quantity of from 0.025 to 0.5 part, in particular from 0.05 to 0.3 part, by weight of noble metal, based on 100 parts of O-benzylglycoloylanilide of the formula (F). The catalyst used which comprises noble metal is a catalyst which comprises palladium or platinum, if desired in sulfited form, in particular a supported catalyst of this kind and preferably an active charcoal catalyst of this kind.

The choice of catalyst also depends to a certain extent on the O-benzylglycoloylanilide of the formula (F) which is to be reacted. In the case of halogen-free O-benzylglycoloyanilides, good results are obtained with supported catalysts which comprise palladium or platinum, in particular active charcoal catalysts which comprise palladium or platinum and preferably active charcoal catalysts which comprise palladium. Where the intention is to react halogen-containing O-benzylglycoloylanilides of the formula (F) it is advisable to use specially modified catalysts, such as sulfited or sulfided palladium or platinum supported catalysts, in particular sulfited platinum supported catalysts and preferably sulfited platinum-active charcoal catalysts. The reaction is performed from 0.1 to 5 MPa, in particular from 0.2 to 3 MPa. The O-benzylglycoloylanilide of the formula (F) and hydrogen are normally reacted at from 20° to 100° C. In numerous cases it has been found sufficient to carry out this reaction at from 30° to 80° C.

The catalysts which comprise noble metal usually contain from 1 to 10% by weight, in particular from 2 to 5% by weight, of noble metal, based on the overall catalyst.

Following the reductive debenzylation in accordance with reaction equation (5), the catalyst which comprises noble metal is separated off, for example by filtration, and the compound of the formula (H) which has been formed is distilled off together with any solvent which may have been used. In the form in which the desired glycoloylanilide is produced, it is already a very pure end product which, however, can additionally be purified further by distillation or crystallization, to give products which are generally almost completely pure by analysis.

For the acylation and benzylation reactions described by reaction equations (2), (3) and (4), suitable solvents are those mentioned for the first reaction equation, albeit with the restriction that alcohols cannot be used since they may react with acid chlorides (chloroacetyl chloride, O-benzylglycoloyl chlorides of the formula (K)) and the chloroacetanilides of the formula (D) and may consequently lead to the formation of unwanted by-products.

For the same reason it is not possible to employ compounds of the formula (C) whose radicals $R^1$ and/or $R^2$ and/or whose radicals $X^2$ contain free hydroxyl groups in the corresponding acylation or benzylation stage, in accordance with reaction equations (2), (3) and (4). These hydroxyl groups must be protected beforehand, for example by acetylation.

The present invention also relates to new O-benzylglycoloylanilides of the formula (F)

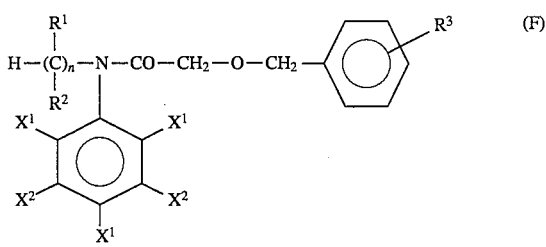

in which $R^1$ and $R^2$ are H, alkyl, hydroxyalkyl, alkoxyalkyl or acyloxyalkyl having in each case 1 to 4 carbon atoms in the alkyl moiety, $R^3$ is H, halogen, alkyl or alkoxy having in each case 1 to 4 carbon atoms in the alkyl moiety, $X^1$ independently at each occurrence is H, halogen, cyano, trifluoromethyl, alkyl or alkoxy having in each case 1 to 4 carbon atoms in the alkyl moiety, $X^2$ independently at each occurrence is H, halogen, cyano, carboxyl, trifluoromethyl, substituted or unsubstituted aminocarbonyl or aminosulfonyl, alkyl, alkoxy or alkoxycarbonyl having in each case 1 to 4 carbon atoms in the alkyl moiety, and n is 0 or 1, in which context at least one of the radicals $X^2$ is different from H if each of the radicals $X^1$ is a $CH_3$ group, or $R^3$ is different from H if n=0 and each of the radicals $X^1$ and $X^2$ is F.

It must be regarded as surprising that the new O-benzylglycoloylanilides of the formula (F) can be used to obtain the desired glycoloylanilides of the formula (G) by means of a simple reaction (debenzylation) with virtually complete conversion and very high selectivity, in accordance with reaction equation (5). The only by-product, formed in stoichiometric quantities, is the compound (toluene or toluene derivative) of the formula (H), which can either be returned to the process for the preparation of the benzyl alcohol of the formula (E) or, if the process according to the invention is carried out in the compound of the formula (H) as solvent, can be used to make up for the solvent losses which occur in the course of regeneration and recovery. The catalyst which comprises noble metal which is used in the debenzylation can be reused a number of times in the reaction.

The present invention further relates to a process for the preparation of the new O-benzylglycoloylanilides of the abovementioned formula (F). This process comprises reacting a nitrobenzene of the formula (A) with hydrogen and, if desired, with a carbonyl compound of the formula (B) in the presence of a catalyst which comprises noble metal and of a solvent, in accordance with reaction equation (1)

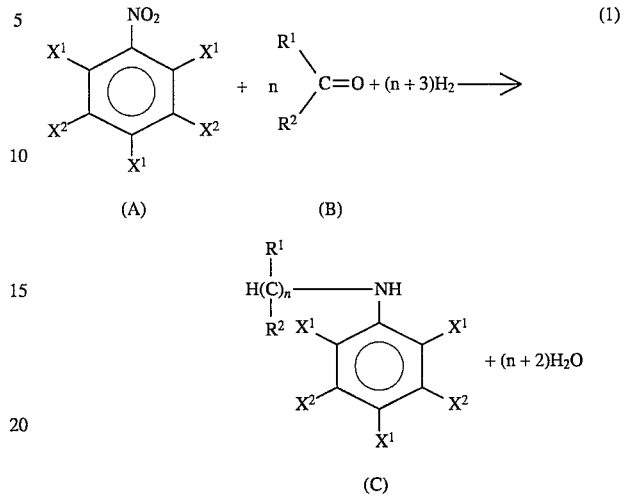

separating off the catalyst and reacting the compound of the formula (C) with chloroacetyl chloride, in accordance with reaction equation (2)

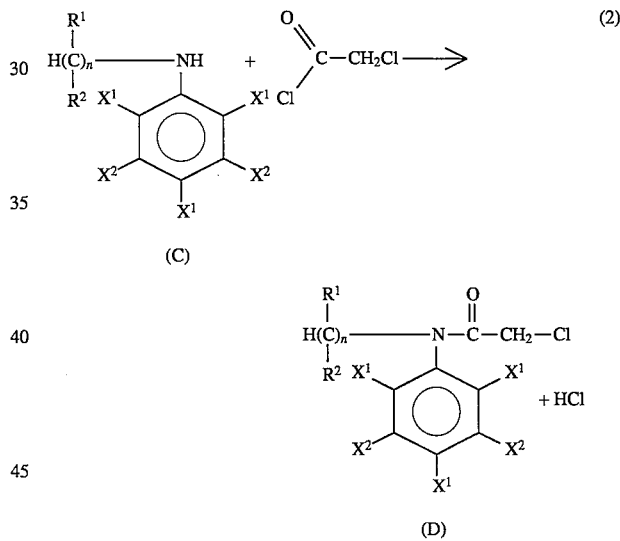

to give a compound of the formula (D), separating off the hydrogen chloride formed, reacting the compound of the formula (D) with a benzyl alcohol of the formula (E) and with a base, in accordance with reaction equation (3)

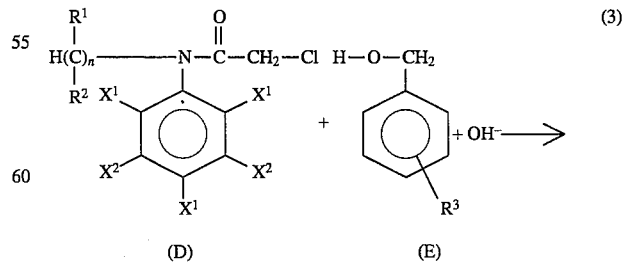

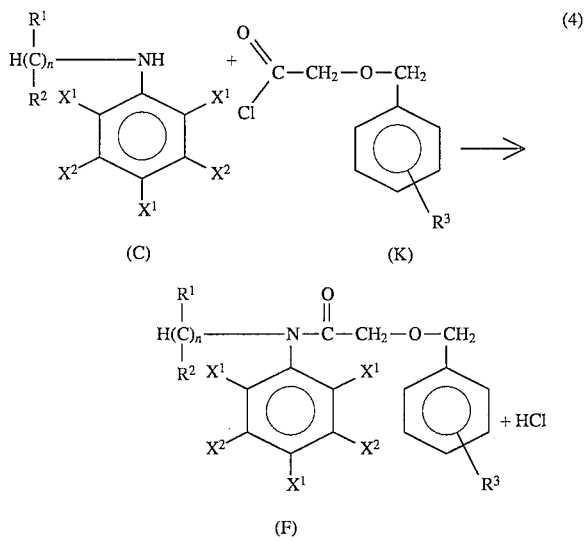

separating off if desired the salt formed from the base and hydrogen chloride, or reacting the compound of the formula (C) with an O-benzylglycoloyl chloride of the formula (K) in which $R^3$ is as defined above, and if desired with a base, in accordance with reaction equation (4)

and separating off if desired the salt formed from the base and hydrogen chloride.

Although the process—starting from nitrobenzenes of the formula (A)—involves a number of stages, it surprisingly makes the new O-benzylglycoloylanilides of the formula (F) accessible not only in a very high yield but also in very high purity. Another advantage of this process is that it is unnecessary to isolate and purify each individual intermediate formed in the course of the synthesis so that it can be processed further in purified form thereafter. Instead, it is possible as desired or required to omit one or more of these isolation steps and the following purification of the particular intermediate. The consequence of this is that the corresponding reaction steps in the process have a particularly simple configuration and the process can be carried out without any great complexity.

In the most favorable case the process according to the invention can be carried out for the preparation of the new O-benzylglycoloylanilides of the formula (F) using a single solvent, in the manner of a one-pot process, without isolation and purification of the respective intermediates. This process variant constitutes a particularly advantageous embodiment of the process which is easy to carry out industrially and requires only the isolation of the catalyst which comprises noble metal and, if desired, of the salts formed, for example by filtration, and the removal of any water of reaction which is present as a heterogeneous phase. If the catalyst which comprises noble metal is employed in the form of a fixed bed, then its isolation from the respective reaction mixture is also dispensed with.

The O-benzylglycoloylanilide of the formula (F) can be processed further in isolated form. However, it is also possible to dispense with such an isolation, as already mentioned above, and to convert the reaction mixture comprising the O-benzylglycoloylanilide directly, without isolating the O-benzylglycoloylanilide of the formula (F), into the corresponding glycoloylanilide of the formula (G), in accordance with reaction equation (5).

The examples which follow demonstrate the invention without limiting it.

EXPERIMENTAL SECTION

Example 1a

Preparation of 4-fluoro-N-isopropylaniline 520 parts of toluene, 423 parts (3 mol) of 4-fluoronitrobenzene, 192 parts (3.3 mol) of acetone and 8 parts of catalyst (5% Pt on charcoal, water-moist, water content 50%) are placed in a hydrogenation autoclave. After the gas space has been flushed three times with each of nitrogen and hydrogen, the mixture is heated to from 80°=0 to 85° C. with stirring and reduced at a hydrogen pressure of from 0.2 to 1.0 MPa. When after about 2 hours the uptake of hydrogen falls sharply, the pressure is raised to 2.0 MPa and stirring is continued at 85° C for 30 minutes until there is no longer any drop in pressure. The batch is cooled to 60° C., the autoclave is let down and flushed with nitrogen, and the catalyst is filtered off on a pressure filter at from 50° to 60° C. The aqueous phase is separated off from the filtrate and toluene is distilled off until the water content of the solution is <0.02%. The solution is processed further in accordance with Example 2.

Alternatively, the solution can be worked up by distillation and the product isolated. Yield 97–98%; purity by GC: $\geq 99.2\%$; boiling point: 91° to 92° C./10 torr.

Example 1b

Preparation of 4-fluoro-N-isopropylaniline

In accordance with Example 1a but using 333 parts (3 mol) of 4-fluoroaniline instead of 4-fluoronitrobenzene, reduction is carried out at from 80° to 85° C. and at a hydrogen pressure of from 1.0 to 2.0 MPa.

The reaction mixture is worked up and processed further as indicated in Example 1a.

Example 2

Preparation of 4-fluoro-N-isopropyl-N-chloroacetylaniline 357.5 parts (3.2 mol) of chloroacetyl chloride are added dropwise over the course of 2 hours at from 10° to 20° C. to 920 parts of 4-fluoro-N-isopropylaniline solution (~3 mol of 4-fluoro-N-isopropylaniline) from Example 1. Stirring is subsequently carried out at 20° C. for one hour and then the majority of the hydrogen chloride formed is removed as a gas by heating to about 90° C.

Subsequently, a pH of 7 is established using sodium hydroxide solution at room temperature, precipitated sodium chloride is removed by filtration and the aqueous phase is separated off.

The solution (1110 parts) is processed further in accordance with Example 3.

Alternatively, the reaction product can be isolated by simple vacuum distillation. Yield: 94%; purity by GC: 98.5%; boiling point: 113°–114° C/1 to 2 torr.

Example 3a

Preparation of 4-fluoro-N-isopropyl-N-benzyloxyacetylaniline 144 parts (3.6 mol) of caustic soda are added continuously or in portions at from 25° to 30° C., with cooling, to about 1110 parts of 4-fluoro-N-isopropyl-N-chloroacetylaniline solution from Example 2, comprising 3 mol of 4-fluoro-N-isopropyl-N-chloroacetylaniline, and 389 parts (3.6 mol) of benzyl alcohol in a stirred apparatus over the course of two hours. The mixture is then heated to 90° C. and subsequently stirred at this temperature for three hours.

The reaction mixture is worked up by cooling to 20 to 50° C., neutralizing it with hydrochloric acid (pH 6 to 7), separating off the salt and washing the salt with three times 60 parts of toluene. The toluene washings and the filtrate are combined. Water, solvent and excess benzyl alcohol are distilled off and the remaining product is subsequently processed further for the preparation of 4-fluoro-N-isopropyl-N-hydroxyacetylaniline.

Alternatively, the benzyloxy derivative can be isolated by vacuum distillation. Yield, based on 4-fluoronitrobenzene employed: 86% of theory; solidification point: 87.8° C; boiling point: 200° C./2 to 3 torr; purity by GC: ≧97%.

Comparison Example 3b

DE-A 29 04 490 describes the reaction of chloroacetanilides with anhydrous sodium acetate to give acetoxyacetanilides and the hydrolysis thereof to give glycoloylanilides.

If this process is transferred to the preparation of acetoxyacetyl-N-isopropyl-4-fluoroanilide, and 229.5 g (1 mol) of chloroacetyl-N-isopropyl-4-fluoroanilide as starting material are reacted with 82 g (1 mol) of anhydrous sodium acetate in 320 ml of toluene at from 115 to 120° C., then the conversion after a reaction time of 10 hours is 10 % max. Even if a ratio of starting material to sodium acetate of 1:3 is employed, no substantial acceleration of the reaction is observed.

Compare Tables I and II below.

TABLE I

| Ratio of starting material to sodium acetate 1:1 | | |
|---|---|---|
| Reaction time in hours | % Starting material* | % Product* |
| 8 | 93 | 4.5 |
| 16 | 87.5 | 9.5 |
| 24 | 84 | 14 |
| 40 | 71 | 28 |
| 75 | 42 | 57.5 |
| 105 | 24 | 75 |
| 150 | 11.5 | 87.5 |
| 175 | 1.7 | 98.0 |
| 180 | 0.5 | 98.9 |

*% by GC analysis without internal standard

TABLE II

| Ratio of starting material to sodium acetate 1:3 | | |
|---|---|---|
| Reaction time in hours | % Starting material* | % Product* |
| 5.5 | 92.2 | 7.0 |
| 11 | 84.5 | 14.8 |
| 20 | 75 | 24.4 |
| 35 | 54 | 45.5 |
| 50 | 32.8 | 66.5 |

TABLE II-continued

| Ratio of starting material to sodium acetate 1:3 | | |
|---|---|---|
| Reaction time in hours | % Starting material* | % Product* |
| 75 | 8.3 | 91.2 |
| 95 | 0.4 | 98.9 |

*% by GC analysis without internal standard

Example 4a

Preparation of N-isopropyl-N-(4-fluorophenyl) glycolamid(4-fluoro-N-isopropyl-N-hydroxyacetylaniline)

301 parts (1 mol) of 4-fluoro-N-isopropyl-N-benzyloxyacetylaniline as the remaining product from Example 3, 600 parts of methanol and 12 parts of palladium catalyst (5% Pd on charcoal, water-moist, water content 50%) are placed in a hydrogenation autoclave. The gas space is flushed with nitrogen and then with hydrogen and then the mixture is heated with stirring to from 70° to 100° C. and reduced at a hydrogen pressure of from 0.5 to 2.0 MPa. After the end of hydrogen uptake, reaction is allowed to continue for about 30 minutes at 100° C. and at a hydrogen pressure of 2.0 MPa. The batch is then cooled to from 30°to 50° C., the autoclave is let down and flushed with nitrogen, and the Pd/C catalyst is separated off on a pressure filter. The solvent is distilled off from the filtrate and the product is isolated by vacuum distillation.

Yield: 191 parts, corresponding to 90.5% of theory, based on the benzyloxy derivative employed. Boiling point: 125° to 126° C. at 2 to 3 torr; solidification point: 59.5° C.; purity by GC: ≧98%.

Example 4b

In place of methanol it is also possible to employ other solvents such as toluene or xylene and carry out the hydrogenolysis as described under 4a.

Examples 5 to 8

Preparation of O-benzylglycoloylanilides of the formula (F)

Example 5

Preparation of O-benzylglycoloyl-4-fluoroanilide

A solution of 4.06 g (0.022 mol) of O-benzylglycoloyl chloride in 20 ml of toluene is added dropwise to a solution of 2.22 g (0.02 mol) of 4-fluoroaniline in 80 ml of toluene in a 250 ml flask at room temperature. The mixture is stirred at 50° C. for 5 h. The contents of the flask are then evaporated to dryness under reduced pressure and the residue is taken up in acetonitrile. The acetonitrile phase is filtered and the filtrate is concentrated to dryness in vacuo. 3 g (58% of theory) of O-benzylglycoloyl-4-fluoroanilide are obtained as a yellow oil with a purity of 97.8% (HPLC). $n_D^{21} = 1.5573$.

O-Benzylglycoloyl-4-fluoroanilide $^1$H-NMR (300 MHz, CDCl$_3$) δ4.1 (s,2H), 4.6 (s,2H), 7.0 (m,2H), 7.3–7.45 (m, 5H), 7.5 (m,2H), 8.3 (s,br, 1H); $^{13}$C-NMR (75 MHz, CDCl$_3$) 167.69, 161.20, 136.53, 133.10, 128.78, 128.28, 128.10, 121.66, 115.54, 73.90, 69.61; $^{19}$F-NMR (282 MHz, CDCl$_3$)-118.16 m; IR (capillary) 3380, 3060, 3030, 2910, 2960, 1735, 1680, 1610, 1535, 1510, 410, 1210, 1115, 835, 795, 740, 700 cm$^{-1}$; MS (70 eV) m/z 260 ([M+H]$^+$), 153, 107, 91 (100%).

Example 6

Preparation of O-benzylglycoloyl-2-methoxyanilide 2.46 g (0.02 mol) of o-anisidine in 80 ml of toluene are placed in a 250 ml flask. At room temperature a solution of 4.06 g (0.022 mol) of O-benzylglycoloyl chloride in 20 ml of toluene is added dropwise. The reaction mixture is subsequently maintained at reflux temperature for 1h. The toluene is stripped off in vacuo and the residue is distilled (up to 190° C. at 2 torr). 3 g (55% of theory) of O-benzylglycoloyl-2-methoxyanilide are obtained as violet oil with a purity of 97.0% (GC). $n_D^{21} = 1.5762$.

O-benzylglycoloyl-2-methoxyanilide $^1$H-NMR (300 MHz, CDCl$_3$) δ3.85 (s,3H), 4.1 (s,2H), 4.65 (s,2H), 6.83–7.05 (m, 3H), 7.24–7.44 (m, 5H), 8.4 (d, 1H, $^3$J =8.0 Hz, $^4$J=1.9 Hz), (s,br, 1H); $^{13}$C-NMR (75 MHz, CDCl$_3$) 167.54, 148.26, 136.97, 128.60, 128.20, 127.77, 7.07, 124.05, 121.11, 119.82, 110.10, 73.68, 70.07, 55.72; IR (capillary) 3390 3065 3030 2940 2900 2840, 1690, 1600, 1530, 1460, 1250, 1115, 750, 700 cm$^{-1}$; MS (70 eV) m/z 271 (M$^+$), 165, 123, 108, 91 (100%).

Example 7

Preparation of O-benzylglycoloyl-4-methoxyanilide 2.46 g (0.02 mol) of p-anisidine in 80 ml of toluene are placed in a 250 ml flask. At room temperature a solution of 4.06 g (0.022 mol) of O-benzylglycoloyl chloride in ml of toluene is added dropwise. The reaction mixture is subsequently heated to a high temperature and boiled under reflux for 1b. The toluene is stripped off in vacuo and the residue is distilled at 200° C. and 2 torr. 3 g (55% of theory) of O-benzylglycoloyl-4-methoxyanilide are obtained as pale violet crystals with a melting point of 68.5° C. and a purity of 100% (GC).

O-benzylglycoloyl-4-methoxyanilide $^1$H-NMR (300 MHz, DMSO) δ3.7 (s,3H), 4.1 (s,2H), 4.6 (s, 2H), 6.9 (m, 2H), 7.25–7.45 (m, 5H), 7.55 (m, 2H), 9.6 (s, 1H); $^{13}$C-NMR (75 MHz, DMSO) 167.53, 155.59, 137.84, 11.63, 128.39, 127.92, 127.76, 121.50, 113.88, 72.53, 69.60, 55.28; IR (KBr) 3300, 3010, 2950, 2830, 1665, 595, 1520 1240 1100 820 cm$^{-1}$; MS (70 eV) m/z 271 (M$^+$, 100%), 165, 150, 121, 91.

Example 8

Preparation of O-benzylglycoloyl-3,5-dimethylanilide 1.48 g (0.012 mol) of 3,5-dimethylaniline in 80 ml of toluene are placed in a 250 ml flask. At 50° C. a solution of 2.50 g (0.014 mol) of O-benzylglycoloyl chloride in 20 ml of toluene is added dropwise. The mixture is subsequently heated at reflux temperature for 3 h, cooled to room temperature and extracted by shaking with saturated sodium hydrogen carbonate solution and water. The organic phase is dried over sodium sulfate and the toluene is stripped off in vacuo. Further volatile constituents are removed in vacuo in a bulb-tube distillation (up to 250° C., 3 torr). The distillation residue comprises 2.15 g (67% of theory) of O-benzylglycoloyl-3,5-dimethylanilide as an orange oil with a purity of 94.3% (GC). $n_D^{21} = 1.5768$.

O-benzylglycoloyl-3,5-dimethylanilide $^1$H-NMR (300 MHz, CDCl$_3$) δ2.3 (s,6H), 4.1 (s,2H), 4.6 (s,2H), 6.8 (m, 1H), 7.2 (s,2H), 7.3–7.5 (m, 5H), 8.2 (s,br, 1H); $^{13}$C-NMR (75 MHz, CDCl$_3$) δ167.37, 138.74, 136.97, 136.68, 128.74, 128.39, 128.04, 126.28, 117.61, 73.78, 69.76, 21.34; IR (capillary) 3400, 3300, 3030, 2920, 2860, 1690, 1615, 1545, 1100, 840, 740, 700 cm$^{-1}$; MS (70 eV) m/z 269 (M$^+$), 210, 163 (100%), 134, 121, 105, 91, 77.

We claim:

1. A process for the preparation of glycoloylanilides of the formula (G)

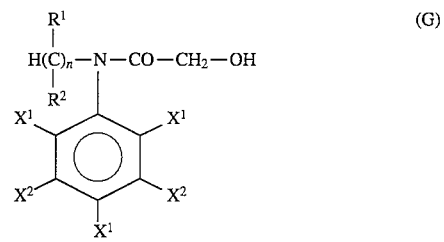

which comprises reacting a nitrobenzene of the formula (A) in which X$^1$ independently at each occurrence is H, halogen, cyano, trifluoromethyl, alkyl or alkoxy having in each case 1 to 4 carbon atoms in the alkyl moiety, and X$^2$ independently at each occurrence is H, halogen, cyano, carboxyl, trifluoromethyl, substituted or unsubstituted aminocarbonyl or aminosulfonyl, alkyl, alkoxy or alkoxycarbonyl having in each case 1 to 4 carbon atoms in the alkyl moiety, and n is 0 or 1, with hydrogen and, if desired, with a carbonyl compound of the formula (B) in which R$^1$ and R$^2$ are H, alkyl, hydroxyalkyl, alkoxyalkyl or acyloxyalkyl having in each case 1 to 4 carbon atoms in the alkyl moiety, in the presence of a catalyst which comprises noble metal and of a solvent, in accordance with reaction equation (1)

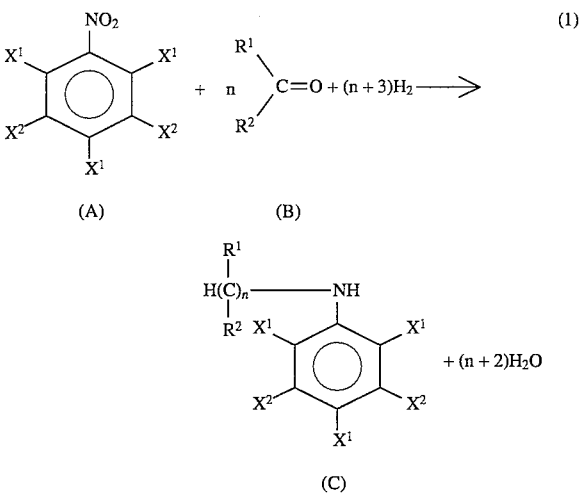

separating off the catalyst and reacting the compound of the formula (C) with chloroacetyl chloride, in accordance with reaction equation (2)

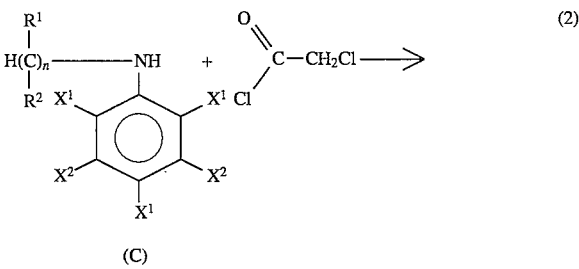

-continued

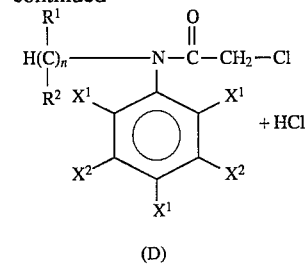
(D)

to give a compound of the formula (D), separating off the hydrogen chloride formed, reacting the compound of the formula (D) with a benzyl alcohol of the formula (E) in which $R^3$ is H, halogen, alkyl or alkoxy having in each case 1 to 4 carbon atoms, and with a base, in accordance with reaction equation (3)

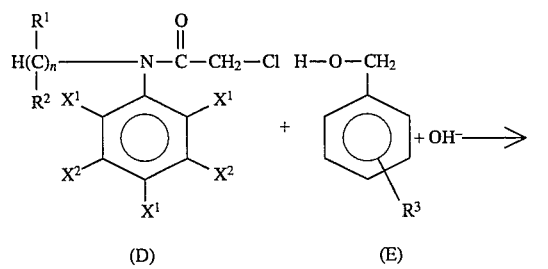

(D)      (E)

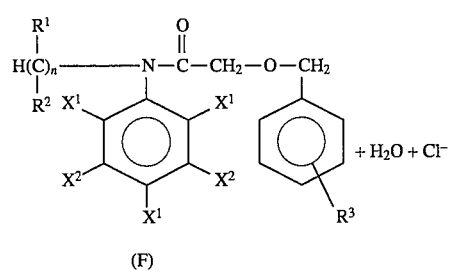

(F)

separating off if desired the salt formed from the base and hydrogen chloride, or reacting the compound of the formula (C) with an O-benzylglycoloyl chloride of the formula (K) in which $R^3$ is as defined above, and if desired with a base, in accordance with reaction equation (4)

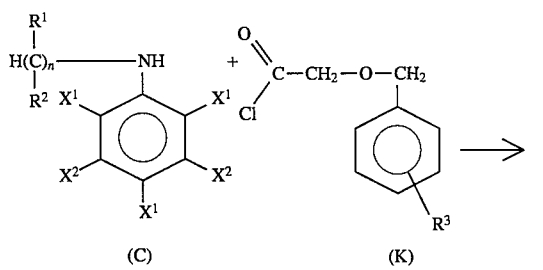

(C)      (K)

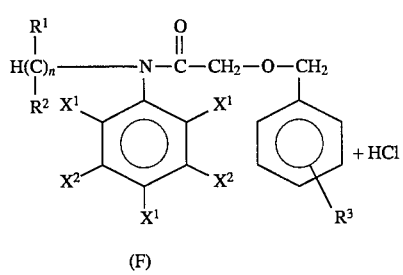

(F)

separating off if desired the salt formed from the base and hydrogen chloride, and reacting the O-benzylglycoloylanilide of the formula (F), in the presence of a catalyst which contains noble metal, with hydrogen, in accordance with reaction equation (5)

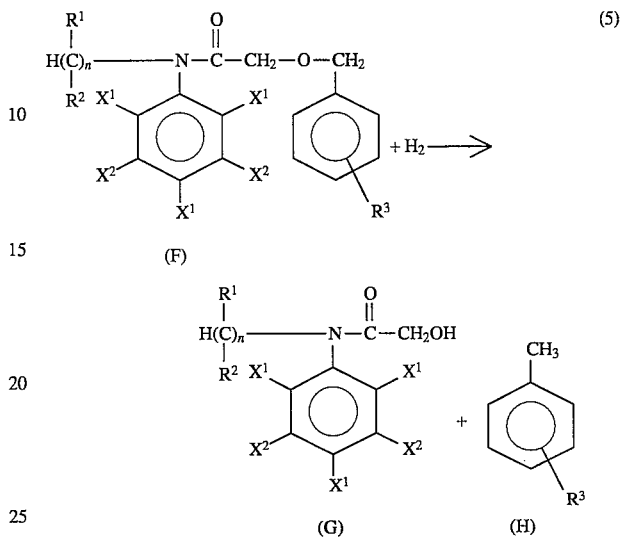

(G)      (H)

separating off the compound of the formula (H) which is formed and isolating the glycoloylanilide of the formula (G).

2. The process as claimed in claim 1, wherein a nitrobenzene of the formula (A) is employed in which $X^1$ independently at each occurrence is H, fluorine, chlorine or trifluoromethyl and $X^2$ independently at each occurrence is H, fluorine, chlorine, trifluoromethyl or substituted or unsubstituted aminocarbonyl.

3. The process as claimed in claim 1, wherein the nitrobenzene of formula (A) is reacted with hydrogen at from 0.1 to 5 MPa.

4. The process as claimed in claim 1, wherein the nitrobenzene of the formula (A) and the carbonyl compound of the formula (B) are employed in a molar ratio of 1:(1.0 to 3.5).

5. The process as claimed in claim 1, wherein the catalyst, which comprises from 1 to 10% by weight of noble metal, is employed in a quantity of from 0.01 to 0.3 part by weight of noble metal, based on 100 parts of nitrobenzene of the formula (A).

6. The process as claimed in claim 1, wherein the catalyst which comprises noble metal employed is a supported catalyst which comprises palladium or platinum, if desired in sulfited or sulfided form.

7. The process as claimed in claim 1, wherein the solvent employed is toluene, any of the various isomeric xylenes, a mixture thereof, any of the various isomeric halotoluenes, a mixture thereof or a compound of the formula (H).

8. The process as claimed in claim 1, wherein the nitrobenzene is reacted at from 20° to 100° C.

9. The process as claimed in claim 1, wherein the reaction mixture which comprises a compound of the formula (C) is reacted directly, without isolating the compound of the formula (C), with chloroacetyl chloride.

10. The process as claimed in claim 1, wherein the compound of the formula (C) is reacted with chloroacetyl chloride at from 0° to 150° C.

11. The process as claimed in claim 1, wherein the compound of the formula (C) and chloroacetyl chloride are reacted in a molar ratio of 1:(1.0 to 1.5).

12. The process as claimed in claim 1, wherein the hydrogen chloride formed is removed by boiling it off, by addition of a base, or by both boiling it off and addition of a base.

13. The process as claimed in claim 1, wherein the hydrogen chloride formed is removed by boiling it off.

14. The process as claimed in claim 1, wherein the reaction mixture which comprises the compound of the formula (D) is reacted directly, without isolating the compound of the formula (D), with the benzyl alcohol of the formula (E).

15. The process as claimed in claim 1, wherein the benzyl alcohol employed is a compound of the formula (E) in which $R^3$ is H, chlorine, methyl or methoxy.

16. The process as claimed in claim 1, wherein the compound of the formula (D) and the benzyl alcohol of the formula (E) are employed in a molar ratio of 1:1 (1 to 1.5).

17. The process as claimed in claim 1, wherein the compound of the formula (D) is reacted at from 20° to 200° C.

18. The process as claimed in claim 1, wherein the compound of the formula (D) and the base are reacted in a molar ratio of 1:(1.0 to 1.5) with the benzyl alcohol of the formula (E).

19. The process as claimed in claim 1, wherein an alkali metal hydroxide or an alkali metal carbonate is employed as base.

20. The process of claimed in claim 1, wherein the reaction mixture which comprises the compound (C) is reacted directly, without isolating the compound of the formula (C), with an O-benzylglycoloyl chloride of the formula (K).

21. The process as claimed in claim 1, wherein an O-benzylglycoloyl chloride of the formula (K) is employed in which $R^3$ is H, chlorine, methyl or methoxy.

22. The process as claimed in claim 1, wherein the compound of the formula (C) and the O-benzylglycoloyl chloride of the formula (K) are reacted in a molar ratio of 1:1 (1 to 1.15).

23. The process as claimed in claim 1, wherein the compound of the formula (C) is reacted with the O-benzylglycoloyl chloride of the formula (K) at from 20° to 150° C.

24. The process as claimed in claim 1, wherein the hydrogen chloride formed when the compound of the formula (C) is reacted with the O-benzylglycoloyl chloride of the formula (K) is separated by boiling it out, by addition of base, or by both boiling it out and addition of a base.

25. The process as claimed in claim 1, wherein the compound of the formula (C) is reacted with the O-benzylglycoloyl chloride of the formula (K) with the addition of an alkali metal hydroxide and/or alkali metal carbonate as base.

26. The process as claimed in claim 1, wherein the reaction mixture which comprises the O-benzylglycoloylanilide of the formula (F) is reacted with hydrogen directly, without isolating the O-benzylglycoloylanilide of the formula (F).

27. The process as claimed in claim 1, wherein a catalyst which comprises from 1 to 10% by weight of noble metal is employed n a quantity of from 0.025 to 0.5 part by weight of noble metal, based on 100 parts of O-benzylglycoloylanilide of the formula (F).

28. The process as claimed in claim 1, wherein the O-benzylglycoloylanilide of the formula (F) is reacted with hydrogen in the presence of a catalyst which comprises noble metal consisting of a supported catalyst comprising palladium or platinum, if desired in sulfited form.

29. The process as claimed in claim 1, wherein the O-benzylglycoloylanilide of the formula (F) is reacted at from 0.1 to 5 MPa.

30. The process as claimed in claim 1, wherein the O-benzylglycoloylanilide of the formula (F) is reacted at from 20° to 100° C.

31. A process for the preparation of an O-benzylglycoloylanilide of the formula (F), as indicated in claim 31, which comprises reacting a nitrobenzene of the formula (A) with hydrogen and, if desired, with a carbonyl compound of the formula (B) in the presence of a catalyst which comprises noble metal and of a solvent, in accordance with reaction equation (1)

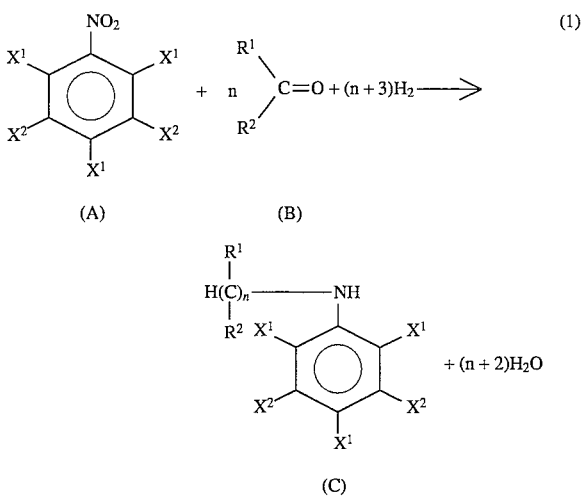

separating off the catalyst and reacting the compound of the formula (C) with chloroacetyl chloride, in accordance with reaction equation (2)

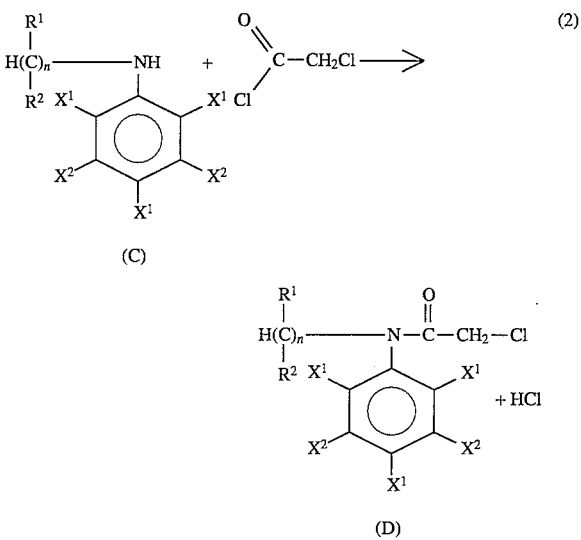

to give a compound of the formula (D), separating off the hydrogen chloride formed, reacting the compound of the formula (D) with a benzyl alcohol of the formula (E) and with a base, in accordance with reaction equation (3)

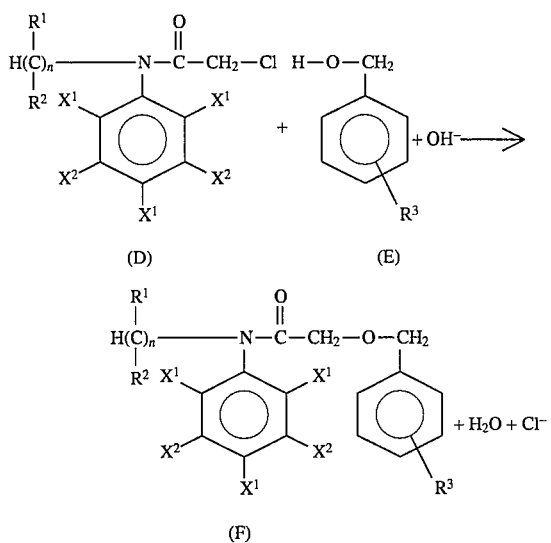

separating off if desired the salt formed from the base and hydrogen chloride, or reacting the compound of the formula (C) with an O-benzylglycoloyl chloride of the formula (K) in which $R^3$ is as defined above, and if desired with a base, in accordance with reaction equation (4)

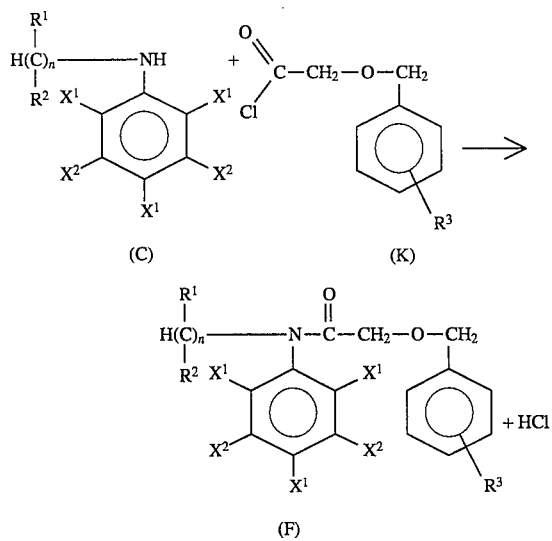

and separating off if desired the salt formed from the base and hydrogen chloride.

32. The process as claimed in claim 1, wherein the nitrobenzene of formula (A) is reacted with hydrogen at from 0.2 to 3 MPa.

33. The process as claimed in claim 1, wherein the nitrobenzene of formula (A) and the carbonyl compound of the formula (B) are employed in a molar ratio of 1:(1.01 to 2.5).

34. The process as claimed in claim 1, wherein the nitrobenzene of formula (A) and the carbonyl compound of the formula (B) are employed in a molar ratio of 1:(1.05 to 1.5).

35. The process as claimed in claim 1, wherein the catalysts comprises from 2 to 5% by weight of noble metal, and is employed in a quantity of from 0.025 to 0.15 part by weight of noble metal, based on 100 parts of nitrobenzene of the formula (A).

36. The process as claimed in claim 1, wherein the catalyst is an active charcoal catalyst which comprises palladium or platinum which may be sulfited or sulphided.

37. The process as claimed in claim 1, wherein the nitrobenzene is reacted at from 60° to 90° C.

38. The process as claimed in claim 1, wherein the compound of the formula (C) is reacted with chloroacetyl chloride at from 20° to 100° C.

39. The process as claimed in claim 1, wherein the compound of the formula (C) and chloroacetyl chloride are reacted in a molar ratio of from 1:(1.05 to 1.15).

40. The process as claimed in claim 1, wherein the compound of the formula (D) and the benzyl alcohol of the formula (E) are employed in a molar ratio of from 1:(1.0 to 1.2).

41. The process as claimed in claim 1, wherein the compound of the formula (D) is reacted at from 20° to 150° C.

42. The process as claimed in claim 1, wherein the compound of the formula (D) and the base are reacted in a molar ratio of from 1:(1.0 to 1.2) with the benzyl alcohol of the formula (E).

43. The process as claimed in claim 1, wherein the compound of the formula (C) and the O-benzylglycoloyl chloride of the formula (K) are reacted in a molar ratio of 1.(1.05 to 1.5).

44. The process as claimed in claim 1, wherein the compound of the formula (C) is reacted with the O-benzylglycoloyl chloride of the formula (K) at from 50° to 130° C.

45. The process as claimed in claim 1, wherein a catalyst which comprises from 2 to 5% by weight of noble is employed in a quantity of from 0.05 to 0.3 part by weight of noble metal, based on 100 parts of O-benzylglycoloylanilide of the formula (F).

46. The process as claimed in claim 1, wherein the O-benzylglycoloylanilide of the formula (F) is reacted at from 0.2 to 3 MPa.

47. The process as claimed in claim 1, wherein the O-benzylglycoloylanilide of the formula (F) is reacted at from 30° to 80° C.

* * * * *

UNITED STATES PATENT AND TRADEMARK OFFICE
CERTIFICATE OF CORRECTION

PATENT NO. : 5,616,799
DATED : April 1, 1997
INVENTOR(S) : Siegfried Planker, et. al.

It is certified that error appears in the above-identified patent and that said Letters Patent is hereby corrected as shown below:

In claim 1 (column 17, line 13), please change "compound of- the formula" to read --compound of the formula--.

In claim 16 (column 19, line 15), please change "1:1(1 to 1.5)" to read --1:(1 to 1.5).

In claim 22 (column 19, lines 35 to 36), please change "1:1(1 to 1.15)" to read --1:(1 to 1.15).

In claim 27 (column 19, line 59) please change "employed n" to read --employed in--.

UNITED STATES PATENT AND TRADEMARK OFFICE
CERTIFICATE OF CORRECTION

PATENT NO. : 5,616,799
DATED : April 1, 1997
INVENTOR(S) : Siegfried Planker, et. al.

It is certified that error appears in the above-identified patent and that said Letters Patent is hereby corrected as shown below:

In claim 31 (column 20, line 10) please change "in claim 31" to read --claim 1--.

In claim 43 (column 22, line 37) please change "1.(1.05 to 1.5)" to read --1:(1.05 to 1.5)--.

In claim 45 (column 22, line 43) please change "noble is" to read --noble metal is--.

Signed and Sealed this

Thirteenth Day of January, 1998

BRUCE LEHMAN

Attest:

Attesting Officer

Commissioner of Patents and Trademarks